US012766248B2

(12) United States Patent
Stokes

(10) Patent No.: US 12,766,248 B2
(45) Date of Patent: Oct. 20, 2026

(54) DISPENSING DEVICE FOR WEARABLE DRUG DELIVERY DEVICE

(71) Applicant: Insulet Corporation, Acton, MA (US)

(72) Inventor: Jeffrey H. Stokes, Harvard, MA (US)

(73) Assignee: INSULET CORPORATION, Acton, MA (US)

( * ) Notice: Subject to any disclaimer, the term of this patent is extended or adjusted under 35 U.S.C. 154(b) by 887 days.

(21) Appl. No.: 17/727,407

(22) Filed: Apr. 22, 2022

(65) Prior Publication Data

US 2022/0339346 A1 Oct. 27, 2022

Related U.S. Application Data

(60) Provisional application No. 63/178,607, filed on Apr. 23, 2021.

(51) Int. Cl.
*A61M 5/142* (2006.01)
*A61M 5/145* (2006.01)
(Continued)

(52) U.S. Cl.
CPC .... *A61M 5/14224* (2013.01); *A61M 5/14216* (2013.01); *A61M 5/14248* (2013.01);
(Continued)

(58) Field of Classification Search
CPC .......... A61M 5/14212; A61M 5/14216; A61M 5/16809; A61M 2205/0266;
(Continued)

(56) References Cited

U.S. PATENT DOCUMENTS

| | | | |
|---|---|---|---|
| 1,441,508 | A | 1/1923 | Jensen |
| 2,198,666 | A | 4/1940 | Gruskin |

(Continued)

FOREIGN PATENT DOCUMENTS

| | | | |
|---|---|---|---|
| CA | 606281 | A | 10/1960 |
| CN | 1375338 | A | 10/2002 |

(Continued)

OTHER PUBLICATIONS

International Search Report and Written Opinion for PCT/US2018/014351, mailed on Jun. 4, 2018, 9 pages.

(Continued)

*Primary Examiner* — Wesley G Harris
(74) *Attorney, Agent, or Firm* — Goodwin Procter LLP

(57) ABSTRACT

Embodiments of the present disclosure relate to techniques, processes, devices or systems for pump devices for providing a fixed volume of fluid, which is delivered and refilled within one pumping cycle. In one approach, a wearable drug delivery device may include a reservoir for storing a liquid drug, and a delivery pump device including a drive mechanism coupled to the reservoir. The drive mechanism may include a housing having a pump chamber fluidly connected with a channel chamber, an inlet channel operable to deliver the liquid drug from the reservoir to the channel chamber, and an outlet channel operable to expel the liquid drug from the channel chamber. The drive mechanism may further include a resilient sealing member sealing the pump chamber, and a plunger adjacent the resilient sealing member, wherein the plunger is operable to enter the pump chamber to displace the liquid drug from the pump chamber.

17 Claims, 8 Drawing Sheets

(51) Int. Cl.
*A61M 5/168* (2006.01)
*A61M 5/172* (2006.01)

(52) U.S. Cl.
CPC ........ *A61M 5/1454* (2013.01); *A61M 5/1456* (2013.01); *A61M 2005/14208* (2013.01); *A61M 5/16809* (2013.01); *A61M 5/1723* (2013.01); *A61M 2205/0266* (2013.01)

(58) Field of Classification Search
CPC .......... A61M 5/14244; A61M 5/14586; A61M 5/1456; A61M 5/14224; A61M 5/14248; A61M 5/1454; A61M 5/1723; A61M 2005/14208
See application file for complete search history.

(56) References Cited

U.S. PATENT DOCUMENTS 2,752,918 A 7/1956 Uytenbogaar
3,176,712 A 4/1965 Ramsden
3,297,260 A 1/1967 Barlow
3,464,359 A 9/1969 King
3,885,662 A 5/1975 Schaefer
3,946,732 A 3/1976 Hurscham
3,947,692 A 3/1976 Payne
3,993,061 A 11/1976 OLeary
4,108,177 A 8/1978 Pistor
4,152,098 A 5/1979 Moody et al.
4,210,173 A 7/1980 Choksi et al.
4,221,219 A 9/1980 Tucker
4,257,324 A 3/1981 Stefansson et al.
4,268,150 A 5/1981 Chen
4,277,226 A * 7/1981 Archibald ................ F04B 7/00 604/245
4,313,439 A 2/1982 Babb et al.
4,371,790 A 2/1983 Manning et al.
4,417,889 A 11/1983 Choi
4,424,720 A 1/1984 Bucchianeri
4,435,173 A 3/1984 Siposs et al.
4,475,905 A 10/1984 Himmelstrup
4,493,709 A * 1/1985 Smith ............... A61M 5/16809 604/246
4,498,843 A 2/1985 Schneider et al.
4,507,115 A 3/1985 Kambara et al.
4,551,134 A 11/1985 Slavik et al.
4,562,751 A 1/1986 Nason et al.
4,567,549 A 1/1986 Lemme
4,585,439 A 4/1986 Michel
4,601,707 A 7/1986 Albisser et al.
4,634,427 A 1/1987 Hannula et al.
4,671,429 A 6/1987 Spaanderman et al.
4,678,408 A 7/1987 Nason et al.
4,684,368 A 8/1987 Kenyon
4,685,903 A 8/1987 Cable et al.
4,755,169 A 7/1988 Sarnoff et al.
4,766,889 A 8/1988 Trick et al.
4,808,161 A 2/1989 Kamen
4,840,542 A * 6/1989 Abbott ............. A61M 5/14224 417/9
4,846,797 A 7/1989 Howson et al.
4,858,619 A 8/1989 Toth
4,898,579 A 2/1990 Groshong et al.
4,908,017 A 3/1990 Howson et al.
4,944,659 A 7/1990 Labbe et al.
4,969,874 A 11/1990 Michel et al.
4,991,743 A 2/1991 Walker
5,007,458 A 4/1991 Marcus et al.
5,020,325 A 6/1991 Henault
5,062,841 A 11/1991 Siegel
5,147,311 A 9/1992 Pickhard
5,178,609 A 1/1993 Ishikawa
5,205,819 A 4/1993 Ross et al.
5,213,483 A 5/1993 Flaherty et al.
5,222,362 A 6/1993 Maus et al.
5,236,416 A 8/1993 McDaniel et al.
5,261,882 A 11/1993 Sealfon
5,261,884 A 11/1993 Stern et al.
5,277,338 A 1/1994 Divall et al.
5,281,202 A 1/1994 Weber et al.
5,346,476 A 9/1994 Elson
5,364,342 A 11/1994 Beuchat et al.
5,388,615 A 2/1995 Edlund et al.
5,433,710 A 7/1995 VanAntwerp et al.
5,503,628 A 4/1996 Fetters et al.
5,520,661 A 5/1996 Lal et al.
5,533,389 A 7/1996 Kamen et al.
5,582,593 A 12/1996 Hultman
5,618,269 A 4/1997 Jacobsen et al.
5,628,309 A 5/1997 Brown
5,637,095 A 6/1997 Nason et al.
5,665,070 A 9/1997 McPhee
5,713,875 A 2/1998 Tanner, II
5,747,350 A 5/1998 Sattler
5,748,827 A 5/1998 Holl et al.
5,776,103 A 7/1998 Kriesel et al.
5,779,676 A 7/1998 Kriesel et al.
5,785,688 A 7/1998 Joshi et al.
5,797,881 A 8/1998 Gadot
5,800,397 A 9/1998 Wilson et al.
5,807,075 A 9/1998 Jacobsen et al.
5,839,467 A 11/1998 Saaski et al.
5,891,097 A 4/1999 Saito et al.
5,897,530 A 4/1999 Jackson
5,906,597 A 5/1999 McPhee
5,911,716 A 6/1999 Rake et al.
5,919,167 A 7/1999 Mulhauser et al.
5,957,890 A 9/1999 Mann et al.
5,961,492 A 10/1999 Kriesel et al.
5,971,963 A 10/1999 Choi
6,019,747 A 2/2000 McPhee
6,050,457 A 4/2000 Arnold et al.
6,068,615 A 5/2000 Brown et al.
6,159,188 A 12/2000 Laibovitz et al.
6,174,300 B1 1/2001 Kriesel et al.
6,190,359 B1 2/2001 Heruth
6,200,293 B1 3/2001 Kriesel et al.
6,352,522 B1 3/2002 Kim et al.
6,363,609 B1 4/2002 Pickren
6,375,638 B2 4/2002 Nason et al.
6,474,219 B2 11/2002 Klitmose et al.
6,485,461 B1 11/2002 Mason et al.
6,485,462 B1 11/2002 Kriesel
6,488,652 B1 12/2002 Weijand et al.
6,520,936 B1 2/2003 Mann
6,527,744 B1 3/2003 Kriesel et al.
6,537,249 B2 3/2003 Kriesell et al.
6,539,286 B1 3/2003 Jiang
6,569,115 B1 5/2003 Barker et al.
6,595,956 B1 7/2003 Gross et al.
6,656,158 B2 12/2003 Mahoney et al.
6,699,218 B2 3/2004 Flaherty et al.
6,723,072 B2 4/2004 Flaherty et al.
6,740,059 B2 5/2004 Flaherty
6,749,407 B2 6/2004 Xie et al.
6,851,260 B2 2/2005 Mernoe
6,883,778 B1 4/2005 Newton et al.
7,018,360 B2 3/2006 Flaherty et al.
7,104,275 B2 9/2006 Dille
7,128,727 B2 10/2006 Flaherty et al.
7,137,964 B2 11/2006 Flaherty
7,160,272 B1 1/2007 Eyal et al.
7,303,549 B2 12/2007 Flaherty
7,771,392 B2 8/2010 De Polo et al.
7,914,499 B2 3/2011 Gonnelli et al.
7,951,114 B2 5/2011 Rush et al.
8,267,921 B2 9/2012 Yodfat et al.
8,382,703 B1 2/2013 Abdelaal
8,499,913 B2 8/2013 Gunter
8,905,995 B2 12/2014 Mernoe
8,920,376 B2 12/2014 Caffey et al.
8,939,935 B2 1/2015 OConnor et al.
9,180,244 B2 11/2015 Anderson et al.
9,192,716 B2 11/2015 Jugl et al.

(56) References Cited

U.S. PATENT DOCUMENTS

| | | | |
|---|---|---|---|
| 9,402,950 B2 | 8/2016 | Dilanni et al. | |
| 9,539,596 B2 | 1/2017 | Ikushima | |
| 10,441,723 B2 | 10/2019 | Nazzaro | |
| 10,695,485 B2 | 6/2020 | Nazzaro | |
| 2001/0016710 A1 | 8/2001 | Nason et al. | |
| 2001/0056258 A1 | 12/2001 | Evans | |
| 2002/0029018 A1 | 3/2002 | Jeffrey | |
| 2002/0032374 A1 | 3/2002 | Holker et al. | |
| 2002/0037221 A1 | 3/2002 | Mastrangelo et al. | |
| 2002/0173769 A1 | 11/2002 | Gray et al. | |
| 2002/0173830 A1 | 11/2002 | Starkweather et al. | |
| 2003/0040715 A1 | 2/2003 | DAntonio et al. | |
| 2003/0055380 A1 | 3/2003 | Flaherty | |
| 2003/0097092 A1 | 5/2003 | Flaherty | |
| 2003/0109827 A1 | 6/2003 | Lavi et al. | |
| 2003/0163097 A1 | 8/2003 | Fleury et al. | |
| 2003/0198558 A1 | 10/2003 | Nason et al. | |
| 2003/0199825 A1 | 10/2003 | Flaherty | |
| 2004/0010207 A1 | 1/2004 | Flaherty et al. | |
| 2004/0064088 A1 | 4/2004 | Gorman et al. | |
| 2004/0068224 A1 | 4/2004 | Couvillon, Jr. et al. | |
| 2004/0069044 A1 | 4/2004 | Lavi et al. | |
| 2004/0092865 A1 | 5/2004 | Flaherty et al. | |
| 2004/0094733 A1 | 5/2004 | Hower et al. | |
| 2004/0153032 A1 | 8/2004 | Garribotto et al. | |
| 2005/0020980 A1 | 1/2005 | Inoue et al. | |
| 2005/0165363 A1 | 7/2005 | Judson et al. | |
| 2005/0203461 A1 | 9/2005 | Flaherty et al. | |
| 2005/0238507 A1 | 10/2005 | Dilanni et al. | |
| 2005/0273059 A1 | 12/2005 | Mernoe | |
| 2005/0277882 A1 | 12/2005 | Kriesel | |
| 2006/0041229 A1 | 2/2006 | Garibotto et al. | |
| 2006/0079765 A1 | 4/2006 | Neer et al. | |
| 2006/0155210 A1 | 7/2006 | Beckman et al. | |
| 2006/0173439 A1 | 8/2006 | Thorne et al. | |
| 2006/0178633 A1 | 8/2006 | Garibotto et al. | |
| 2006/0253085 A1 | 11/2006 | Geismar et al. | |
| 2006/0282290 A1 | 12/2006 | Flaherty et al. | |
| 2007/0005018 A1 | 1/2007 | Tekbuchava | |
| 2007/0073236 A1 | 3/2007 | Merno et al. | |
| 2007/0088271 A1 | 4/2007 | Richards | |
| 2007/0118405 A1 | 5/2007 | Campbell et al. | |
| 2007/0191716 A1* | 8/2007 | Goldberger ...... | A61B 5/150992 600/481 |
| 2007/0282269 A1 | 12/2007 | Carter et al. | |
| 2008/0004515 A1 | 1/2008 | Jennewine | |
| 2008/0051738 A1 | 2/2008 | Griffin | |
| 2008/0114304 A1 | 5/2008 | Nalesso et al. | |
| 2008/0172028 A1 | 7/2008 | Blomquist | |
| 2008/0243211 A1 | 10/2008 | Cartwright et al. | |
| 2008/0294040 A1 | 11/2008 | Mohiuddin et al. | |
| 2009/0024083 A1 | 1/2009 | Kriesel et al. | |
| 2009/0062767 A1 | 3/2009 | Van Antwerp et al. | |
| 2009/0198215 A1 | 8/2009 | Chong et al. | |
| 2009/0278875 A1 | 11/2009 | Holm et al. | |
| 2009/0326472 A1 | 12/2009 | Carter et al. | |
| 2010/0036326 A1 | 2/2010 | Matusch | |
| 2010/0152658 A1 | 6/2010 | Hanson et al. | |
| 2010/0198183 A1* | 8/2010 | Lanigan ................. | H01Q 9/265 604/406 |
| 2010/0241066 A1 | 9/2010 | Hansen et al. | |
| 2011/0054399 A1 | 3/2011 | Chong et al. | |
| 2011/0073620 A1 | 3/2011 | Verrilli | |
| 2011/0144586 A1 | 6/2011 | Michaud et al. | |
| 2011/0180480 A1 | 7/2011 | Kloeffel et al. | |
| 2011/0230833 A1 | 9/2011 | Andman et al. | |
| 2012/0078161 A1 | 3/2012 | Masterson et al. | |
| 2012/0172817 A1 | 7/2012 | Bruggemann et al. | |
| 2012/0209207 A1 | 8/2012 | Gray et al. | |
| 2013/0006213 A1 | 1/2013 | Arnitz et al. | |
| 2013/0017099 A1 | 1/2013 | Genoud | |
| 2013/0064701 A1 | 3/2013 | Konishi | |
| 2013/0177455 A1 | 7/2013 | Kamen et al. | |
| 2013/0178803 A1 | 7/2013 | Raab | |
| 2013/0245545 A1 | 9/2013 | Arnold et al. | |
| 2013/0267932 A1 | 10/2013 | Franke et al. | |
| 2013/0296792 A1 | 11/2013 | Cabiri | |
| 2014/0018730 A1 | 1/2014 | Muller-Pathle | |
| 2014/0127048 A1 | 5/2014 | Dilanni et al. | |
| 2014/0128839 A1 | 5/2014 | Dilanni et al. | |
| 2014/0142508 A1 | 5/2014 | Dilanni et al. | |
| 2014/0148784 A1 | 5/2014 | Anderson et al. | |
| 2014/0171901 A1 | 6/2014 | Langsdorf et al. | |
| 2015/0041498 A1 | 2/2015 | Kakiuchi et al. | |
| 2015/0051487 A1 | 2/2015 | Uber et al. | |
| 2015/0057613 A1 | 2/2015 | Clemente et al. | |
| 2015/0064036 A1 | 3/2015 | Eberhard | |
| 2015/0137017 A1 | 5/2015 | Ambrosina et al. | |
| 2015/0202386 A1 | 7/2015 | Brady et al. | |
| 2015/0290389 A1 | 10/2015 | Nessel | |
| 2015/0297825 A1 | 10/2015 | Focht et al. | |
| 2016/0008549 A1 | 1/2016 | Plumptre et al. | |
| 2016/0025544 A1 | 1/2016 | Kamer | |
| 2016/0055842 A1 | 2/2016 | Defranks et al. | |
| 2016/0082242 A1 | 3/2016 | Burton et al. | |
| 2016/0129190 A1 | 5/2016 | Haitsuka | |
| 2016/0193423 A1 | 7/2016 | Bilton | |
| 2016/0213851 A1 | 7/2016 | Weibel et al. | |
| 2017/0021096 A1 | 1/2017 | Cole et al. | |
| 2017/0021137 A1 | 1/2017 | Cole | |
| 2017/0100541 A1 | 4/2017 | Constantineau et al. | |
| 2017/0216516 A1 | 8/2017 | Dale | |
| 2017/0239415 A1 | 8/2017 | Hwang et al. | |
| 2017/0290975 A1 | 10/2017 | Barmaimon et al. | |
| 2018/0021521 A1 | 1/2018 | Sanchez | |
| 2018/0185579 A1 | 7/2018 | Joseph et al. | |
| 2018/0313346 A1 | 11/2018 | Oakes | |
| 2019/0083698 A1* | 3/2019 | Lanigan ............... | G05D 7/0647 |
| 2019/0192782 A1 | 6/2019 | Pedersen et al. | |
| 2019/0365993 A1 | 12/2019 | Staub et al. | |
| 2020/0009315 A1 | 1/2020 | Brouet et al. | |
| 2020/0345931 A1 | 11/2020 | Gray et al. | |

FOREIGN PATENT DOCUMENTS

| | | | | |
|---|---|---|---|---|
| CN | 102498292 B | 7/2015 | | |
| CN | 204972511 U | 1/2016 | | |
| CN | 105764543 B | 7/2016 | | |
| CN | 206175149 U | 5/2017 | | |
| CN | 107096091 A | 8/2017 | | |
| CN | 108472441 A | 8/2018 | | |
| DE | 4200595 A1 | 7/1993 | | |
| DE | 19723648 C1 | 8/1998 | | |
| DE | 102005040344 A1 | 3/2007 | | |
| EP | 0454331 A1 | 10/1991 | | |
| EP | 0789146 A1 | 8/1997 | | |
| EP | 867196 A2 | 9/1998 | | |
| EP | 1065378 A2 | 1/2001 | | |
| EP | 1177802 A1 | 2/2002 | | |
| EP | 1403519 A1 | 3/2004 | | |
| EP | 2397181 A1 | 12/2011 | | |
| EP | 2468338 A1 | 6/2012 | | |
| EP | 2703024 A1 | 3/2014 | | |
| EP | 1874390 B1 | 10/2014 | | |
| EP | 2830499 A1 | 2/2015 | | |
| FR | 2096275 A5 | 2/1972 | | |
| FR | 2455269 A1 | 11/1980 | | |
| FR | 2507637 A1 | 12/1982 | | |
| FR | 2731475 A1 | 9/1996 | | |
| GB | 357139 A | 9/1931 | | |
| GB | 810488 A | 3/1959 | | |
| GB | 875034 A | 8/1961 | | |
| GB | 1204836 A | 9/1970 | | |
| GB | 2008806 A | 6/1979 | | |
| GB | 2077367 A | * 12/1981 | ........ | A61M 5/14224 |
| GB | 2456681 A | 7/2009 | | |
| GB | 2549750 A | 11/2017 | | |
| IL | 46017 A | 11/1977 | | |
| JP | 06063133 A | 3/1994 | | |
| JP | H06296690 A | 10/1994 | | |
| JP | H08238324 A | 9/1996 | | |
| JP | 2004247271 A | 9/2004 | | |
| JP | 2004274719 A | 9/2004 | | |
| JP | 2005188355 A | 7/2005 | | |

(56) References Cited

FOREIGN PATENT DOCUMENTS

| | | | | |
|---|---|---|---|---|
| JP | 2006159228 A | 6/2006 | | |
| JP | 6098988 B2 | 9/2006 | | |
| JP | 2006249130 A | 9/2006 | | |
| JP | 2009514580 A | 4/2009 | | |
| JP | 2017513577 A | 6/2017 | | |
| NL | 1019126 C1 | 4/2003 | | |
| WO | 8101658 A1 | 6/1981 | | |
| WO | 8606796 A1 | 11/1986 | | |
| WO | 9320864 A1 | 10/1993 | | |
| WO | 9415660 A1 | 7/1994 | | |
| WO | 9855073 A1 | 12/1998 | | |
| WO | 9856293 A1 | 12/1998 | | |
| WO | 9910040 A1 | 3/1999 | | |
| WO | 9910049 A1 | 3/1999 | | |
| WO | 9962576 A1 | 12/1999 | | |
| WO | 0029047 A1 | 5/2000 | | |
| WO | 0178812 A1 | 10/2001 | | |
| WO | 0220073 A2 | 3/2002 | | |
| WO | 0226282 A2 | 4/2002 | | |
| WO | 2002076535 A1 | 4/2002 | | |
| WO | 2003097133 A1 | 4/2002 | | |
| WO | 02068823 A1 | 9/2002 | | |
| WO | WO-2004032994 A2 * | 4/2004 | ........... | A61B 5/1411 |
| WO | 2004056412 A2 | 7/2004 | | |
| WO | 2004110526 A1 | 12/2004 | | |
| WO | 2007066152 A2 | 6/2007 | | |
| WO | WO-2007095093 A2 * | 8/2007 | ........... | A61B 5/0024 |
| WO | 2008133702 A1 | 11/2008 | | |
| WO | 2009039203 A2 | 3/2009 | | |
| WO | 2009141005 A1 | 11/2009 | | |
| WO | 2010022069 A2 | 2/2010 | | |
| WO | 2010077279 A1 | 7/2010 | | |
| WO | 2010139793 A1 | 12/2010 | | |
| WO | 2011010198 A2 | 1/2011 | | |
| WO | 2011031458 A1 | 3/2011 | | |
| WO | 2011069935 A2 | 6/2011 | | |
| WO | 2011075042 A1 | 6/2011 | | |
| WO | 2011133823 A1 | 10/2011 | | |
| WO | 2012073032 A1 | 6/2012 | | |
| WO | 2013050535 A2 | 4/2013 | | |
| WO | 2013137893 A1 | 9/2013 | | |
| WO | 2013149186 A1 | 10/2013 | | |
| WO | 2014029416 A1 | 2/2014 | | |
| WO | 2014149357 A1 | 9/2014 | | |
| WO | 2014179774 A1 | 11/2014 | | |
| WO | 2015032772 A1 | 3/2015 | | |
| WO | 2015048791 A1 | 4/2015 | | |
| WO | 2015081337 A2 | 6/2015 | | |
| WO | 2015117854 A1 | 8/2015 | | |
| WO | 2015167201 A1 | 11/2015 | | |
| WO | 2015177082 A1 | 11/2015 | | |
| WO | 2017148855 A1 | 9/2017 | | |
| WO | 2017187177 A1 | 11/2017 | | |
| WO | 2021016452 A1 | 1/2021 | | |

OTHER PUBLICATIONS

Lind et al. "Linear Motion Miniature Actuators." Paper presented at the 2nd Tampere International Conference on Machine Automation, Tampere, Finland (Sep. 1998).
Author Unknown "The Animas R-1000 Insulin Pump—Animas Corporation intends to exit the insulin pump businessand discontinue the manufacturing and sale of Animas® Vibe® and One Touch Ping® insulin bumps." [online], Dec. 1999 [retrieved on Jan. 8, 2019]. Retrieved from the Internet URL: http://www.animaspatientsupport.com/.
Author Unknown, CeramTec "Discover the Electro Ceramic Products CeramTec acquired from Morgan AdvancedMaterials" [online], Mar. 1, 2001 [retrieved on Jan. 8, 2019. Retrieved from the Internet URL: http://www.morgantechnicalceramics.com/.
Vaughan, M.E., "The Design, Fabrication, and Modeling of a Piezoelectric Linear Motor." Master's thesis, Virginia Polytechnic Institute and State University, VA. (2001).
Galante et al., "Design, Modeling, and Performance of a High Force Piezoelectric Inchworm Motor," Journal of Intelligent Material Systems and Structures, vol. 10, 962 -972 (1999).
International Search Report and Written Opinion for International Application No. PCT/US2017/055054, mailed on Jan. 25, 2018, 13 pages.
International Search Report and Written Opinion for International Application No. PCT/US2018/045155, mailed on Oct. 15, 2018, 15 pages.
International Preliminary Report on Patentability for International Application No. PCT/US2017/034811 issued on Nov. 27, 2018, 10 pages.
International Preliminary Report on Patentability for International Patent Application No. PCT/US2017/046508, Feb. 12, 2019, 10 pages.
International Search Report and Written Opinion for International Application No. PCT/US2017/046508, mailed on Jan. 17, 2018, 14 pages.
International Search Report and Written Opinion for International Application No. PCT/US2017/046777, mailed on Dec. 13, 2017, 14 pages.
International Search Report and Written Opinion for International Application No. PCT/US2017/046737, mailed on Dec. 14, 2017, 11 pages.
International Search Report and Written Opinion for International Application No. PCT/US2017/034814, mailed on Oct. 11, 2017, 18 pages.
European Search Report and Written Opinion for the European Patent Application No. EP19177571, dated Oct. 30, 2019, 8 pages.
International Preliminary Report on Patentability for International Patent Application No. PCT/US2018/014351, dated Jul. 23, 2019, 7 pages.
International Preliminary Report on Patentability for International Patent Application No. PCT/US2017/046777, dated Feb. 19, 2019, 8 pages.
International Preliminary Report on Patentability for International Patent Application No. PCT/US2017/046737, dated Feb. 19, 2019, 8 pages.
International Preliminary Report on Patentability for International Patent Application No. PCT/US2017/055054, dated Apr. 9, 2019, 8 pages.
International Search Report and Written Opinion for Application No. PCT/US2017/034811, mailed Oct. 18, 2017, 15 pages.
EPO Search Report received in Application No. 13768938.6, dated Nov. 11, 2015, 8 pages.
International Search Report and Written Opinion for PCT Application No. PCT/US13/34674, mailed Aug. 6, 2013, 17 pages.
International Search Report and Written Opinion for International Application No. PCT/GB2007/004073, Jan. 31, 2008, 8 pages.
International Search Report and Written Opinion for International Patent Application No. PCT/US2019/063615, dated May 3, 2020, 17 pages.
International Preliminary Report on Patentability for International Patent Application No. PCT/US2018/045155, dated Feb. 14, 2020, 10 pages.
International Search Report and Written Opinion for International Patent Application No. PCT/US2019/035756, dated Jul. 31, 2019, 11 pages.
European Search Report and Written Opinion for European Patent Application No. EP20174878, dated Sep. 29, 2020, 4 pages.
Schott web-page image from Jul. 9, 2016, https://www.us.schott.com/pharmaceutical_packaging/english/products/cartridges.html.
International Search Report and Written Opinion for International Patent Application No. PCT/US2021/055581, dated Feb. 8, 2022, 19 pages.
International Search Report and Written Opinion for International Patent Application No. PCT/US2022/011356, dated Apr. 29, 2022, 19 pages.
International Search Report and Written Opinion for International Patent Application No. PCT/US2022/029012, mailed Aug. 19, 2022, 12 pages.
International Search Report and Written Opinion for PCT Application No. PCT/US2019/059854, mailed Aug. 26, 2020, 15 pages.

(56) References Cited

OTHER PUBLICATIONS

International Search Report and Written Opinion, Application No. PCT/US2022/016713, mailed Aug. 5, 2022, 19 pages.

* cited by examiner

DISPENSING DEVICE FOR WEARABLE DRUG DELIVERY DEVICE

RELATED APPLICATIONS

This application claims the benefit of U.S. Provisional Patent Application No. 63/178,607, filed Apr. 23, 2021, the contents of which are incorporated herein by reference in their entirety.

TECHNICAL FIELD

The disclosed embodiments generally relate to medication delivery. More particularly, the disclosed embodiments relate to techniques, processes, systems, and dispensing devices for providing a fixed volume of fluid, which is delivered and refilled within one pumping cycle.

BACKGROUND

Many wearable drug delivery devices include a reservoir for storing a liquid drug. A drive mechanism is operated to expel the stored liquid drug from the reservoir for delivery to a user. Some conventional drive mechanisms use a plunger to expel the liquid drug from the reservoir. Accordingly, the drive mechanism generally has a length equal to a length of the reservoir. And when the reservoir is filled, these wearable drive mechanisms require a length of the drug delivery devices to be significantly larger, for example, about twice the length of the reservoir when the plunger has yet to traverse the length of the reservoir to expel fluid. Increasing the size of the drug delivery devices to accommodate filled reservoirs or pre-filled cartridges and corresponding drive mechanism components leads to bulky devices that are uncomfortable for the user to wear.

Accordingly, there is a need for a simplified system for accurately expelling a liquid drug from a reservoir, which also reduces drug delivery device size.

SUMMARY

This Summary is provided to introduce a selection of concepts in a simplified form that are further described below in the Detailed Description. This Summary is not intended to identify key features or essential features of the claimed subject matter, nor is it intended as an aid in determining the scope of the claimed subject matter.

In some approaches, a wearable drug delivery device may include a wearable drug delivery device having a reservoir configured to store a liquid drug, and a delivery pump device including a drive mechanism coupled to the reservoir for receiving the liquid drug. The drive mechanism may include a housing having a pump chamber fluidly connected with a channel chamber, an inlet channel operable to deliver the liquid drug from the reservoir to the channel chamber, and an outlet channel operable to expel the liquid drug from the channel chamber. The drive mechanism may further include a resilient sealing member sealing the pump chamber, and a plunger adjacent the resilient sealing member, wherein the plunger is operable to enter the pump chamber to displace the liquid drug from the pump chamber.

In some approaches, a drive mechanism of a wearable drug delivery device may include a housing having a pump chamber fluidly connected with a channel chamber, an inlet channel operable to deliver a liquid drug from a reservoir of the wearable drug delivery device to the channel chamber, and an outlet channel operable to expel the liquid drug from the channel chamber. The drive mechanism may further include a resilient sealing member sealing the pump chamber, and a plunger adjacent the resilient sealing member, wherein the plunger is operable to enter the pump chamber to expel the liquid drug from the pump chamber.

Furthermore, in some approaches, a method may include coupling a drive mechanism to a reservoir configured to store a liquid drug, the drive mechanism including a housing having a pump chamber fluidly connected with a channel chamber, an inlet channel operable to deliver the liquid drug from the reservoir to the channel chamber, and an outlet channel operable to expel the liquid drug from the channel chamber. The drive mechanism may further include a resilient sealing member sealing the pump chamber, and a plunger adjacent the resilient sealing member. The method may further include biasing the plunger into the pump chamber to displace the liquid drug from the pump chamber.

BRIEF DESCRIPTION OF THE DRAWINGS

In the drawings, like reference characters generally refer to the same parts throughout the different views. In the following description, various embodiments of the present disclosure are described with reference to the following drawings, in which.

Figure 1:
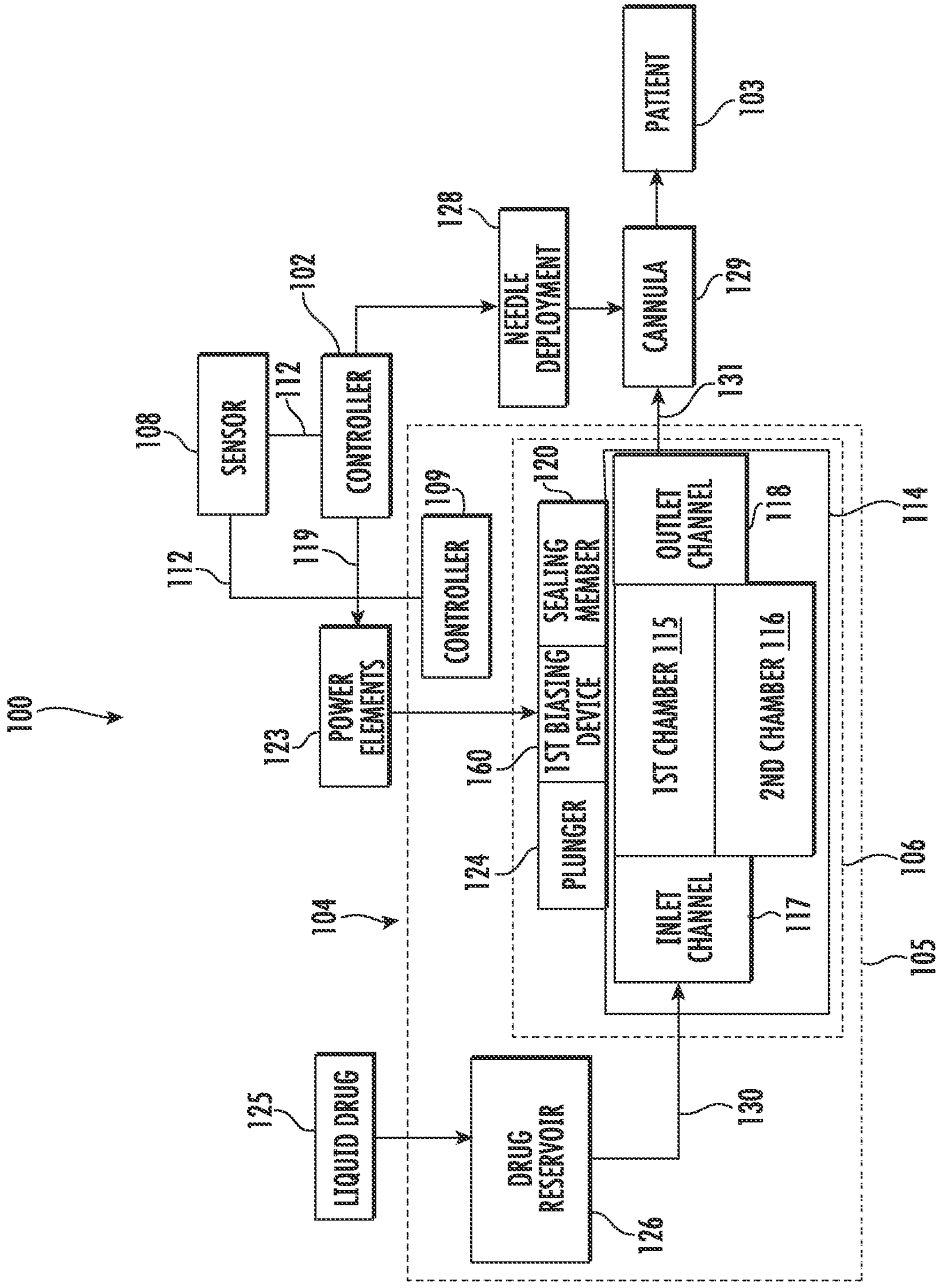
FIG. 1 illustrates a schematic diagram of a drug delivery system according to embodiments of the present disclosure.

The drawings are not necessarily to scale. The drawings are merely representations, not intended to portray specific parameters of the disclosure. The drawings are intended to depict exemplary embodiments of the disclosure, and therefore are not be considered as limiting in scope. Furthermore, certain elements in some of the figures may be omitted, or illustrated not-to-scale, for illustrative clarity. Still furthermore, for clarity, some reference numbers may be omitted in certain drawings.

DETAILED DESCRIPTION

Systems, devices, and methods in accordance with the present disclosure will now be described more fully hereinafter with reference to the accompanying drawings, where one or more embodiments are shown. The systems, devices, and methods may be embodied in many different forms and are not to be construed as being limited to the embodiments set forth herein. Instead, these embodiments are provided so the disclosure will be thorough and complete, and will fully convey the scope of methods and devices to those skilled in the art. Each of the systems, devices, and methods disclosed herein provides one or more advantages over conventional systems, components, and methods.

Embodiments of the present disclosure provide a drive mechanism of a delivery pump device, the drive mechanism including a pump chamber, sealed with a resilient sealing member, and a complimentary shaped plunger operable to be inserted and withdrawn from the pump chamber. When the plunger is moved into the pump chamber, the resilient sealing member deflects and fills the pump chamber completely, thus displacing a liquid drug therefrom. In some embodiments, the liquid drug is provided to a cannula or microneedle array, e.g., via an outlet channel of a housing of the drive mechanism. The volume of the pump chamber may determine the amount of liquid drug dispensed to a patient. As the plunger is moved out of the pump chamber, the liquid drug may be drawn through an inlet channel from a reservoir of the delivery pump device. In some embodiments, aspiration of the pump chamber is facilitated by the elastomeric properties of the resilient sealing member wanting to return to its natural/original shape.

In some embodiments, the inlet and outlet channels may be fluidly connected by a channel chamber. More specifically, the inlet channel may include an inlet chamber and the outlet channel may include an outlet chamber, wherein the channel chamber extends between the inlet chamber and the outlet chamber. In some embodiments, the inlet chamber and the outlet chamber are sealed by one or more resilient sealing members (e.g., a gasket). The gasket may span both the inlet and outlet chambers, allowing the inlet channel to be blocked but allowing fluid to connect from the pump chamber to the outlet chamber. Conversely, the outlet channel can be blocked by the gasket while the inlet channel is connected to the pump chamber.

In some embodiments, the drive mechanism may include a follower coupled to the housing, wherein the follower is moveable relative to the housing to control movement of the plunger. The follower may be moved in one direction by a shape memory alloy (SMA) wire and biased in a second direction by a return spring. Upon activation/contraction of the SMA wire, the follower is brought into contact with the plunger, thus forcing the plunger towards the resilient sealing member. The SMA wire may continue to contract until a tip of the plunger and the resilient sealing member are fully inserted within the pump chamber, and a fixed volume of the liquid drug is forced through the outlet channel. The fixed volume may be a function of internal chamber geometries and SMA stroke.

When the SMA wire is deactivated, the SMA wire will start to relax and the stored energy of the return spring will cause the follower to spring back to an original position. The motion of the follower in turn causes the plunger and the resilient sealing member to move out of the pump chamber, thus creating a negative pressure differential in the pump chamber and the inlet channel, which causes the liquid drug to be drawn back into the pump chamber. The cycle is then repeated by activating the SMA wire. Advantageously, the delivery pump device of the present disclosure enables a fixed volume of fluid to be delivered and refilled without any secondary steps or additional components. Said another way, the system design and material properties of the SMA wire and the resilient sealing member dictate the fluid response into and out of the pump chamber.

In various embodiments, the wearable drug delivery device described herein may include an analyte sensor, such as a blood glucose sensor, and the cannula or microneedle array may be operable in allowing the device to measure an analyte level in a user of the device.

FIG. 1 illustrates a simplified block diagram of an example system 100. The system 100 may be a wearable or on-body drug delivery device and/or an analyte sensor attached to the skin of a patient 103. The system 100 may include a controller 102, a pump mechanism 104 (hereinafter "pump 104"), and a sensor 108. The sensor 108 may be a glucose or other analyte monitor such as, for example, a continuous glucose monitor, and may be incorporated into the wearable device. The sensor 108 may, for example, be operable to measure blood glucose (BG) values of a user to generate a measured BG level signal 112. The controller 102, the pump 104, and the sensor 108 may be communicatively coupled to one another via a wired or wireless communication path. For example, each of the controller 102, the pump 104 and the sensor 108 may be equipped with a wireless radio frequency transceiver operable to communicate via one or more communication protocols, such as Bluetooth®, or the like. As will be described in greater detail herein, the system 100 may also include a delivery pump device (hereinafter "device") 105, which includes a drive mechanism 106 having at least one housing 114 defining a pump chamber 115, a channel chamber 116, an inlet channel 117, and an outlet channel 118. The drive mechanism 106 may further include a resilient sealing member 120 enclosing the pump chamber 115, and a first biasing device 160 (e.g., SMA wire) operable to bias or move a plunger 124 relative to the pump chamber 115, as will be described in greater detail herein. The system 100 may include additional components not shown or described for the sake of brevity.

The controller 102 may receive a desired BG level signal, which may be a first signal, indicating a desired BG level or range for the patient 103. The desired BG level may be stored in memory of a controller 109 on device 105, received from a user interface to the controller 102, or another device, or by an algorithm within controller 109 (or controller 102) that automatically determines a BG level for the patient 103. The sensor 108 may be coupled to the patient 103 and operable to measure an approximate value of a BG level of the user. In response to the measured BG level or value, the sensor 108 may generate a signal indicating the measured BG value. As shown in the example, the controller 102 may also receive from the sensor 108 via a communication path, the measured BG level signal 112, which may be a second signal.

Based on the desired BG level and the measured BG level signal 112, the controller 102 or controller 109 may generate one or more control signals for directing operation of the pump 104. For example, one control signal 119 from the controller 102 or controller 109 may cause the pump 104 to turn on, or activate one or more power elements 123 operably connected with the device 105. As will be described in greater detail herein, in the case where the first biasing device 160 is an SMA wire, activation of the SMA wire by the power element 123 may cause the SMA wire to change shape and/or length, which in turn will change a configuration of the plunger 124 and the resilient sealing member 120. The specified amount of a liquid drug 125 (e.g., insulin, GLP-1, or a co-formulation of insulin and GLP-1; a chemotherapy drug; a blood thinner; or a pain medication) may then be drawn into the pump chamber 115, through the inlet channel 117, in response to a change in pressure due to the change in configuration of the resilient sealing member 120 and the plunger 124. Ideally, the specified amount of the liquid drug 125 may be determined based on a difference between the desired BG level and the actual BG level signal 112. The specified amount of the liquid drug 125 may be determined as an appropriate amount of insulin to drive the measured BG level of the user to the desired BG level. Based on operation of the pump 104, as determined by the control signal 119, the patient 103 may receive the liquid drug from a reservoir 126. The system 100 may operate as a closed-loop system, an open-loop system, or as a hybrid system. In an exemplary closed-loop system, the controller 109 may direct operation of the device 105 without input from the user or controller 102, and may receive BG level signal 112 from the sensor 108. The sensor 108 may be housed within the device 105 or may be housed in a separate device and communicate wirelessly directly with the device 105.

As further shown, the system 100 may include a needle deployment component 128 in communication with the controller 102 or the controller 109. The needle deployment component 128 may include a needle and/or cannula 129 deployable into the patient 103 and may have one or more lumens and one or more holes at a distal end thereof. The cannula 129 may form a portion of a fluid path coupling the patient 103 to the reservoir 126. More specifically, the inlet channel 117 may be coupled to the reservoir 126 by a first fluid path component 130. The first fluid path component 130 may be of any size and shape and may be made from any material. The first fluid path component 130 can allow fluid, such as the liquid drug 125 in the reservoir 126, to be transferred to the device 105 through the inlet channel 117.

As further shown, the outlet channel 118 may be coupled to the cannula 129 by a second fluid path component 131. The second fluid path component 131 may be of any size and shape and may be made from any material. The second fluid path component 131 may be connected to the cannula 129 to allow fluid expelled from the device 105 to be provided to the patient 103. The first and second fluid path components 130 and 131 may be rigid or flexible.

The controller 102/109 may be implemented in hardware, software, or any combination thereof. The controller 102/109 may, for example, be a processor, a logic circuit or a microcontroller coupled to a memory. The controller 102/109 may maintain a date and time as well as other functions (e.g., calculations or the like) performed by processors. The controller 102/109 may be operable to execute an artificial pancreas (AP) algorithm stored in memory (not shown) that enables the controller 102/109 to direct operation of the pump 104. For example, the controller 102/109 may be operable to receive an input from the sensor 108, wherein the input comprises analyte level data, such as blood glucose data or levels over time. Based on the analyte level data, the controller 102/109 may modify the behavior of the pump 104 and resulting amount of the liquid drug 125 to be delivered to the patient 103 via the device 105.

In some embodiments, the sensor 108 may be, for example, a continuous glucose monitor (CGM). The sensor 108 may be physically separate from the pump 104, or may be an integrated component within a same housing thereof. The sensor 108 may provide the controller 102 with data indicative of measured or detected blood glucose levels of the user.

The power element 123 may be a battery, a piezoelectric device, or the like, for supplying electrical power to the device 105. In other embodiments, the power element 123, or an additional power source (not shown), may also supply power to other components of the pump 104, such as the controller 102, memory, the sensor 108, and/or the needle deployment component 128.

In an example, the sensor 108 may be a device communicatively coupled to the controller 102 and may be operable to measure a blood glucose value at a predetermined time interval, such as approximately every 5 minutes, 1 minute, or the like. The sensor 108 may provide a number of blood glucose measurement values to the AP application.

In some embodiments, the pump 104, when operating in a normal mode of operation, provides insulin stored in the reservoir 126 to the patient 103 based on information (e.g., blood glucose measurement values, target blood glucose values, insulin on board, prior insulin deliveries, time of day, day of the week, inputs from an inertial measurement unit, global positioning system-enabled devices, Wi-Fi-enabled devices, or the like) provided by the sensor 108 or other functional elements of the system 100 or pump 104. For example, the pump 104 may contain analog and/or digital circuitry that may be implemented as the controller 102/109 for controlling the delivery of the drug or therapeutic agent. The circuitry used to implement the controller 102/109 may include discrete, specialized logic and/or components, an application-specific integrated circuit, a microcontroller or processor that executes software instructions, firmware, programming instructions or programming code enabling, for example, an AP application stored in memory, or any combination thereof. For example, the controller 102/109 may execute a control algorithm and other programming code that may make the controller 102/109 operable to cause the pump to deliver doses of the drug or therapeutic agent to a user at predetermined intervals or as needed to bring blood glucose measurement values to a target blood glucose value. The size and/or timing of the doses may be pre-programmed, for example, into the AP application by the patient 103 or by a third party (such as a health care provider, a parent or guardian, a manufacturer of the wearable drug delivery device, or the like) using a wired or wireless link, or may be calculated iteratively by the controller 102 or controller 109, such as every 5 minutes.

Although not shown, in some embodiments, the sensor 108 may include a processor, memory, a sensing or measuring device, and a communication device. The memory may store an instance of an AP application as well as other programming code and be operable to store data related to the AP application.

In various embodiments, the sensing/measuring device of the sensor 108 may include one or more sensing elements, such as a blood glucose measurement element, a heart rate monitor, a blood oxygen sensor element, or the like. The sensor processor may include discrete, specialized logic and/or components, an application-specific integrated circuit, a microcontroller or processor that executes software instructions, firmware, programming instructions stored in memory, or any combination thereof.

Figure 2:
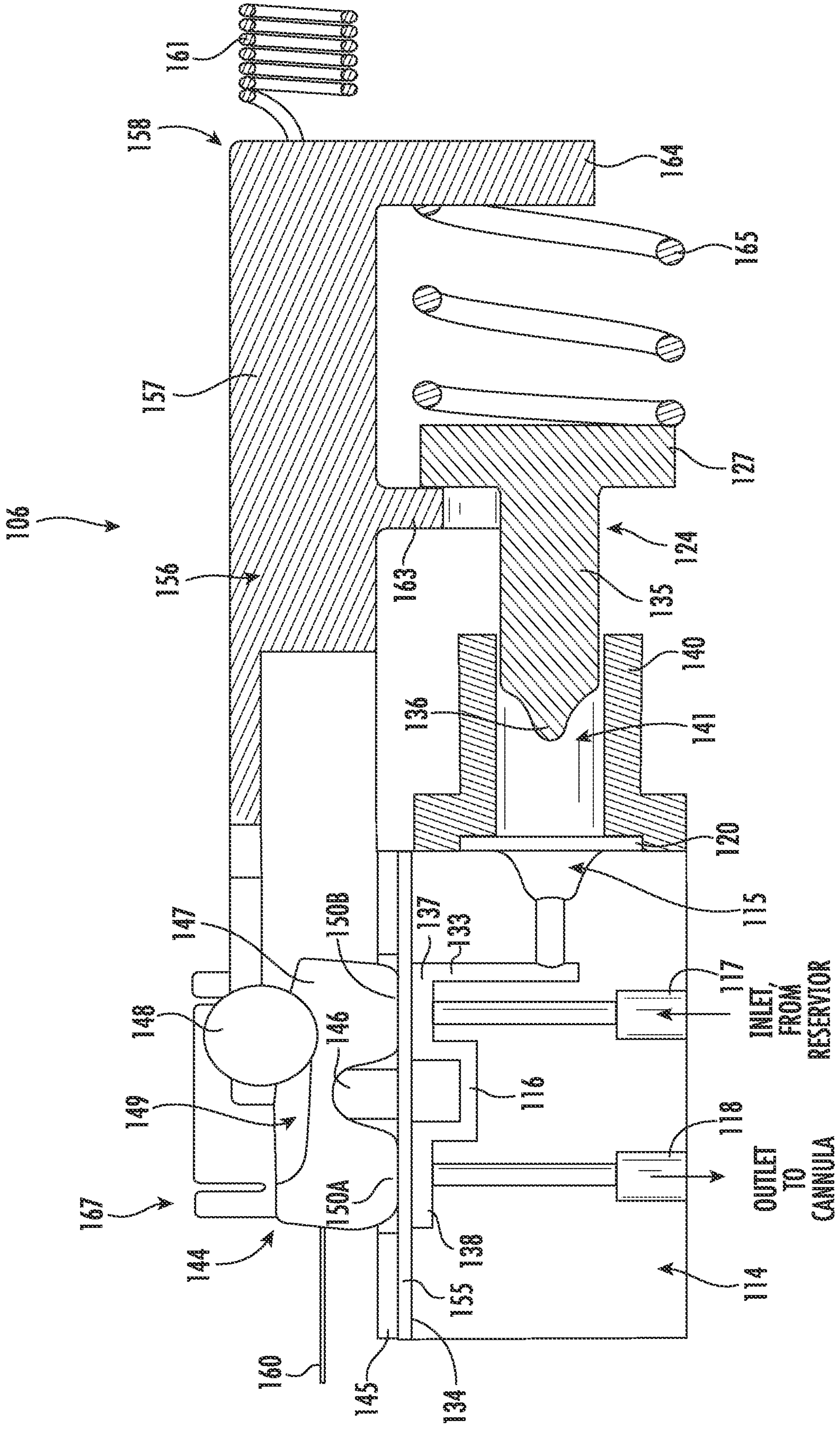
FIG. 2 illustrates a side cross-sectional view of a drive mechanism of a delivery pump device according to embodiments of the present disclosure.

Turning now to FIG. 2, the drive mechanism 106 according to embodiments of the present disclosure will be described in greater detail. As shown, the drive mechanism 106 may include the housing 114 defining the pump chamber 115, the channel chamber 116, the inlet channel 117, and the outlet channel 118. The pump chamber 115 and the channel chamber 116 may be fluidly connected by an internal channel 133. Although non-limiting, the pump chamber 115 may have a bell shape/profile, which compliments the exterior shape/profile of a tip 136 of the plunger 124. The channel chamber 116 may fluidly connect the inlet channel 117 with the outlet channel 118. More specifically, the inlet channel 117 may include an inlet chamber 137 and the outlet channel 118 may include an outlet chamber 138, wherein the channel chamber 116 extends between the inlet chamber 137 and the outlet chamber 138. Although non-limiting, the channel chamber 116 may have a U-shaped profile, as shown, or a substantially straight/horizontal profile.

Coupled to the housing 114, or integrally formed therewith, may be a plunger cylinder 140 defining an internal plunger chamber 141 configured to receive a shaft 135 of the plunger 124. Although not limited to any particular shape or configuration, the plunger 124 may include the tip 136 at a first end and a flange 127 at a second end.

As further shown, the resilient sealing member 120 may be positioned across the pump chamber 115, creating a liquid-tight seal between the internal plunger chamber 141 and the pump chamber 115. In some embodiments, the resilient sealing member 120 is sandwiched between the housing 114 and the plunger cylinder 140. Although non-limiting, the resilient sealing member 120 may be made from a shape memory polymer, such as a polymeric smart material, which has the ability to return from a temporary deformed/compressed shape to a permanent or natural non-deformed/un-compressed shape. For example, the straight/vertical configuration of the resilient sealing member 120 may correspond to its natural or permanent shape.

The drive mechanism 106 may further include a switching device 144 coupled to the housing 114. In some embodiments, the switching device 144 may be a mechanical toggle including a base 145 and a rocker 147 operable to rotate about a fulcrum 146 of the base 145 based on a position of a ball 148 within a slot 149. As shown, the rocker 147 may include a pair of legs 150A, 150B straddling the fulcrum 146 and extending into an opening in the base 145. During operation, one of the legs 150A, 150B of the rocker 147 may be pressed against a second resilient sealing member 155, depending on the position of the rocker 147, to control flow of the liquid drug through the inlet and outlet channels 117, 118. As shown, the second resilient sealing member 155 may extend across the inlet chamber 137 and the outlet chamber 138, thus allowing the inlet channel 117, the outlet channel 118, and the internal channel 133 to be fluidly connected by the channel chamber 116. In some embodiments, the second resilient sealing member 155 may be sandwiched between the housing 114 and the base 145 of the switching device 144. Although non-limiting, the second resilient sealing member 155 may be made from a shape memory polymer, such as a polymeric smart material, which has the ability to return from a temporary deformed/compressed shape to a permanent or natural non-deformed/un-compressed shape. For example, the straight/horizontal configuration of the second resilient sealing member 155 may correspond to its natural or permanent shape.

The drive mechanism 106 may further include a follower 156 coupled to the switching device 144 and to the plunger 124. As shown, the follower 156 may include a body 157 having a first end 167 opposite a second end 158. Coupled to the first end 167 of the body 157 may be the first biasing device 160, (e.g., a SMA wire, motor with lead screw, linear actuator, etc.), and coupled to the second end 158 of the body 157 may be a second biasing device 161 (e.g., return spring). The first biasing device 160 may cause the follower 156 to move in a first direction and the second biasing device 161 may cause the follower 156 to move in a second direction, opposite the first direction.

In a case where the first biasing device 160 is an SMA wire, the power element 132 (FIG. 1) may be activated to energize the SMA wire, which causes the SMA wire to change shape (e.g., contract). More specifically, the activated SMA wire begins to shorten, after having previously been passively relaxed, pulling the follower 156 and the plunger 124 towards the housing 114 as the SMA wire strives to return to its memorized or natural/pre-stressed shape and length. In various embodiments, contraction of the SMA wire may be controlled by increasing or decreasing heat generated by the power element 132. For example, a lower current supplied to the SMA wire may cause the follower 156 to move more slowly than a higher current.

Although non-limiting, the SMA wire may be linear or may generally be V-shaped or U-shaped, with one end of the SMA wire, or a base of the SMA wire (i.e., the area where both legs meet) coupled to the first end 167 of the follower 156. In the latter case, the total force exerted by each leg may be summed, with the total pulling force accordingly doubled for a U or V-shaped arrangement. For a given required total force, thinner SMA wires may accordingly be used, with the electric resistance increasing with decreasing diameter. Further, since the electric resistance depends on the total length of the SMA wire, the electric resistances of a U- or V-shaped arrangement is accordingly double the electric resistance of a single leg of identical diameter. The double leg configuration of the SMA wire accordingly results in a comparatively high electric resistance, which is favorable in order to limit the required current for heating. In other embodiments, alternative folding arrangements are possible, such as a threefold (resulting in an "N-shape") or a fourfold (resulting in an "M-shape").

In some embodiments, the follower 156 may include a first engagement wall 163 operable to engage the flange 127 of the plunger 124 and a second engagement wall 164 in abutment with a plunger spring 165. As shown, the plunger spring 165 may be compressed between the second engagement wall 164 and the flange 127 of the plunger 124 to bias the plunger 124 towards the first engagement wall 163. The second biasing device 161 may be directly coupled to the second engagement wall 164.

FIGS. 3A-3D illustrate the drive mechanism 106 at various stages of a filling and pumping cycle according to embodiments of the present disclosure. Although not demonstrated, the drive mechanism 106 may first be primed to fill the pump chamber 115, e.g., by repeatedly cycling in fluid and expelling air from the inlet channel 117, the pump chamber 115, the channel chamber 116, and the outlet channel 118. At the stage demonstrated in FIG. 3A, the first biasing device 160 (e.g., SMA wire) may be inactive, which allows the follower 156 to move away from the housing 114, e.g., along direction 'D1,' in response to a force from the second biasing device 161. Movement of the follower 156 may cause the ball 148 of the switching device 144 to roll towards the plunger 124, which in turn may cause the rocker 147 to rotate (e.g., clockwise) about the fulcrum 146 and the leg 150B of the rocker 147 to engage the second resilient sealing member 155. Due to the force from the leg 150B, the second resilient sealing member 155 may be deformed or depressed into the inlet chamber 137 and against an entrance 168 of the inlet channel 117. A seal is created therebetween to prevent further flow of the liquid drug 125 from the inlet channel 117.

Furthermore, movement of the follower 156 may cause the first engagement wall 163 to engage the flange 127 of the plunger 124, which in turn may cause the plunger 124 to be retracted relative to the pump chamber 115 and the resilient sealing member 120. A force from the plunger spring 165 may maintain contact between the first engagement wall 163 and the flange 127 of the plunger 124 as the plunger 124 moves along direction 'D1'. An amount of the liquid drug 125 within the pump chamber 115 may change as the resilient sealing member 120 changes configuration. For example, in response to movement by the resilient sealing member 120 into the flat/vertical position shown, the liquid drug 125 may be drawn through the inlet channel 117 and into the pump chamber 115. More specifically, negative pressure created in the pump chamber 115 by the reconfiguration of the resilient sealing member 120 and the plunger 124 causes the liquid drug 125 to flow through the internal channel 133 and into the pump chamber 115 while the inlet channel 117 remains closed at the entrance 168.

Figure 3A:
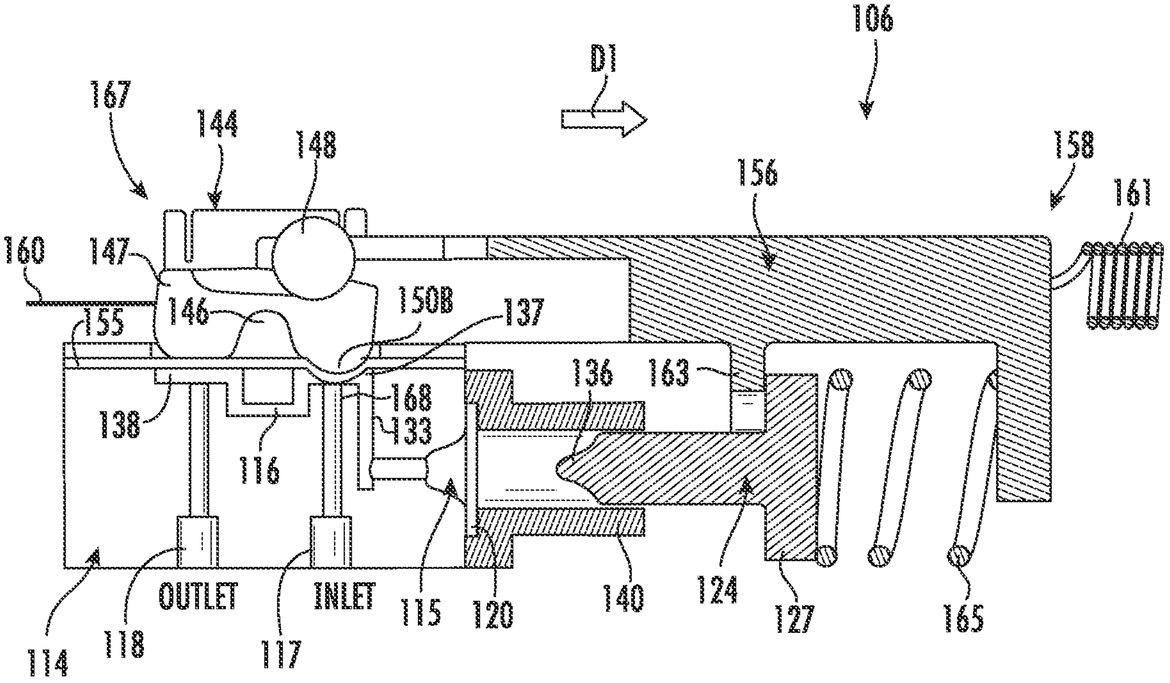
FIGS. 3A-3D illustrate side cross-sectional views of a drive mechanism of a delivery pump device according to embodiments of the present disclosure.
Figure 3B:
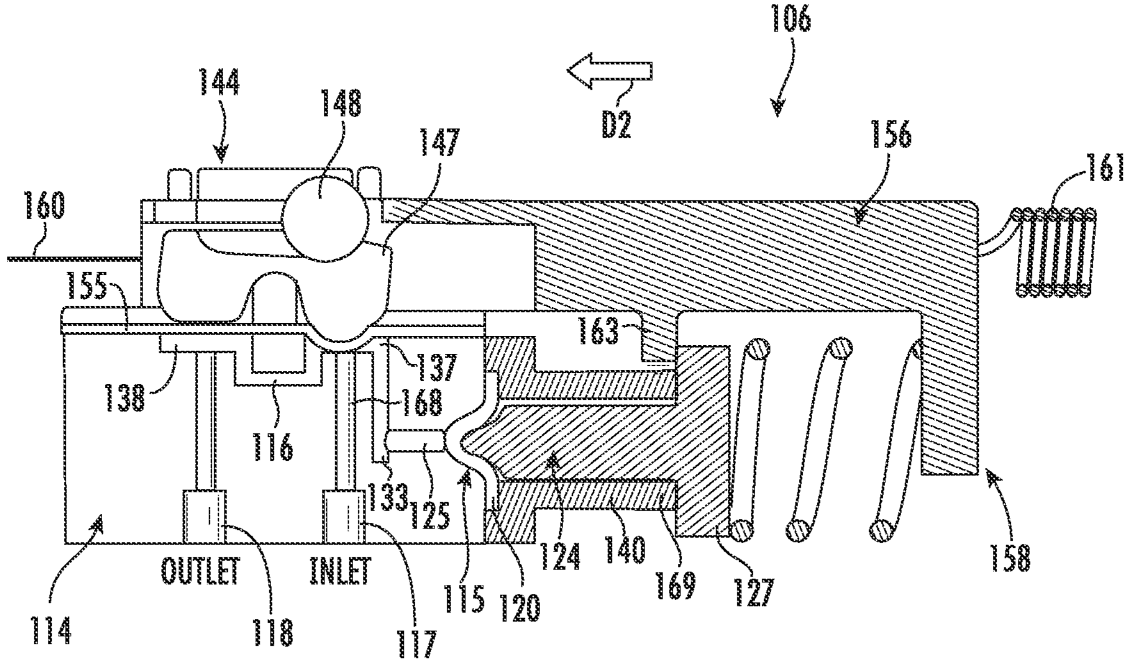

As demonstrated in FIG. 3B, the first biasing device 160 may be activated, e.g., in response to a current received from the power element 132 (FIG. 1), which causes the follower 156 to move towards the housing 114, e.g., along direction 'D2,' overcoming the force of the second biasing device 161. The follower 156 and the plunger 124 may move towards the housing 114 until the flange 127 of the plunger 124 abuts an end 169 of the plunger cylinder 140 and the tip 136 of the plunger 124 is inserted into the pump chamber 115. With the entrance 168 to the inlet channel 117 closed by the second resilient sealing member 155, the liquid drug 125 is displaced from the pump chamber 115 and the internal channel 133, and forced towards the channel chamber 116 for delivery to the patient via the outlet chamber 138 and the outlet channel 118.

Figure 3C:
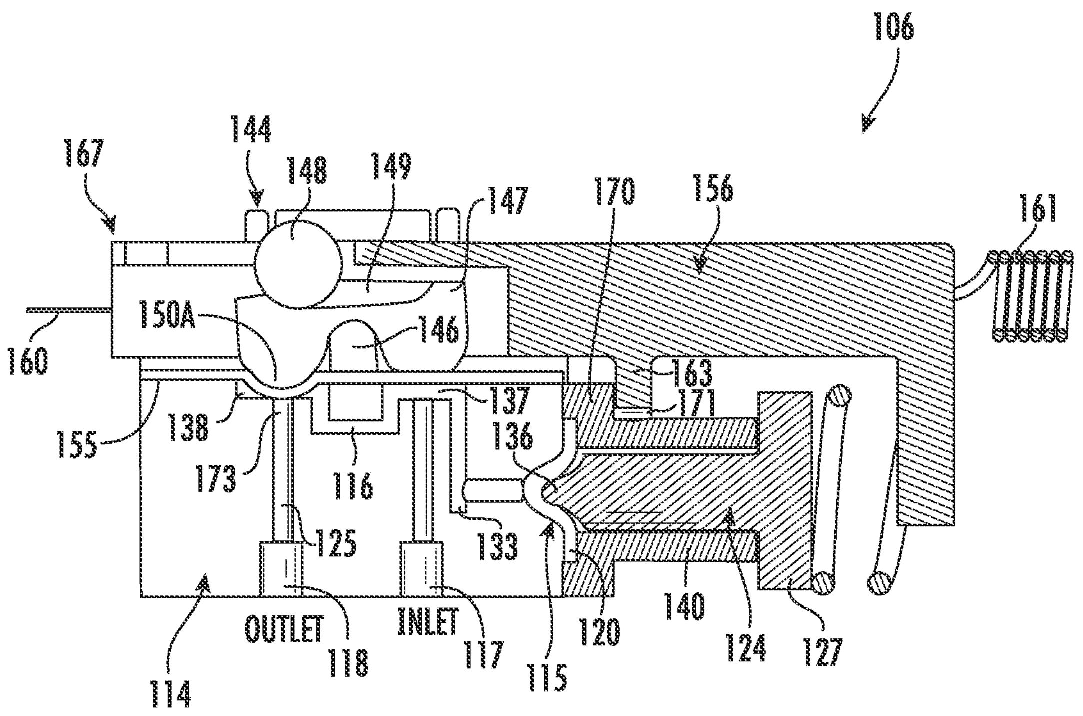

As demonstrated in FIG. 3C, activation of the first biasing device 160 continues until the first engagement wall 163 of the follower 156 separates from the flange 127 of the plunger 124 and moves into contact with a plunger wall flange 170 of the plunger cylinder 140. In some embodiments, the first engagement wall 163 may have an opening or recess 171, which allows the first engagement wall 163 to pass over an exterior of the plunger cylinder 140. Movement of the follower 156 into the configuration shown causes the switching device 144 to transition from a first position (shown in FIGS. 3A-3B) to a second position in which leg 150A of the rocker 147 depresses the second resilient sealing member 155 into the outlet chamber 138 and against an entrance 173 of the outlet channel 118. More specifically, the ball 148 may move within the slot 149 towards the first end 167 of the follower 156 until the rocker 147 rotates (e.g., counterclockwise) about the fulcrum 146. As a result, a liquid-tight seal is created across the entrance 173 of the outlet channel 118 to prevent further flow of the liquid drug 125 from the channel chamber 116 to the outlet channel 118.

In some embodiments, deactivation of the SMA wire of the first biasing device 160, e.g., by the controller 102 (FIG. 1), may occur following expiration of a predetermined time period triggered by the initial activation of the SMA wire. The predetermined time period may be sufficient to allow a controlled dose (e.g., 0.05 mL or 0.025 mL) of the liquid drug 125 to enter and then be discharged from the pump chamber 115, and then delivered to the patient 103 via the cannula 129.

Figure 3D:
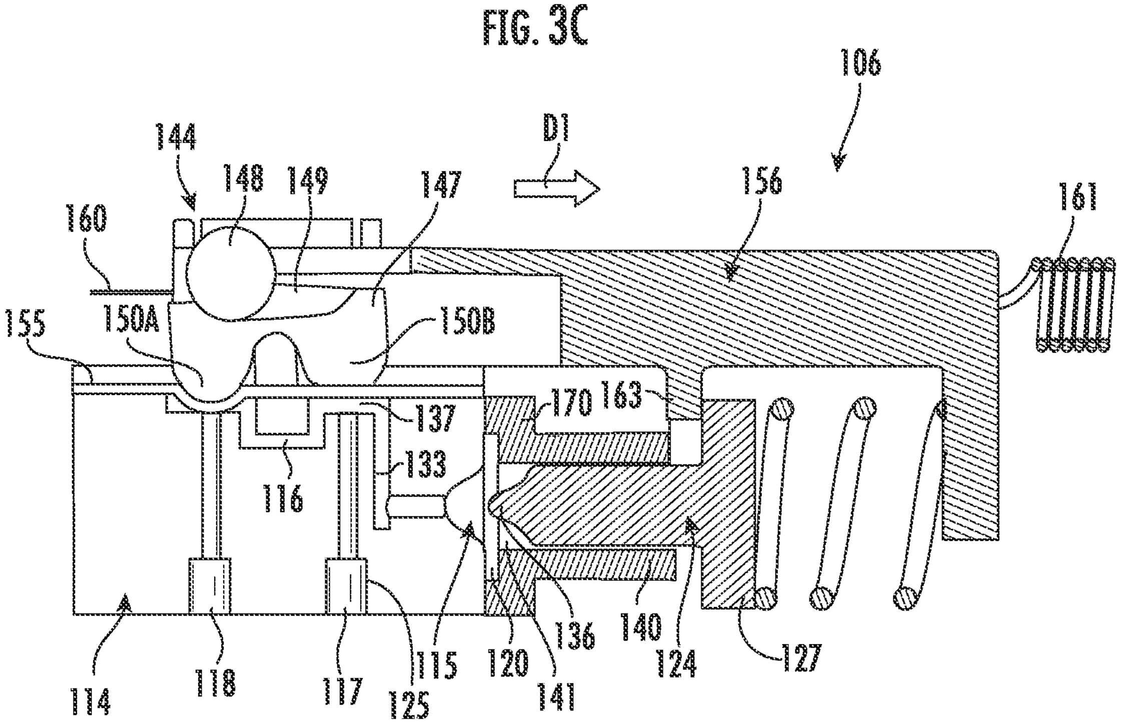

As demonstrated in FIG. 3D, the second biasing device 161 may pull the follower 156 away from the housing 114, e.g., along direction 'D1,' which causes the first engagement wall 163 to move from the plunger wall flange 170 of the plunger cylinder 140 to the flange 127 of the plunger 124. In some embodiments, when the first biasing device 160 is an SMA wire, current to the SMA wire is decreased or discontinued to relax/elongate the SMA wire, which allows the force of the second biasing device 161 pull the follower 156 along direction 'D1.' As shown, a force on the flange 127 from the first engagement wall 163 may cause the tip 136 of the plunger 124 to retract from the pump chamber 115. Negative pressure created as the plunger 124 is retracted from the internal plunger chamber 141 causes the liquid drug 125 to be drawn through the inlet channel 117 again. More specifically, an amount of the liquid drug 125 within the pump chamber 115 may change as the resilient sealing member 120 changes configuration. For example, in response to movement by the resilient sealing member 120 into the flat/vertical position shown, the liquid drug will be drawn through the inlet channel 117 and into the pump chamber 115 via the inlet chamber 137 and the internal channel 133.

Figure 4A:
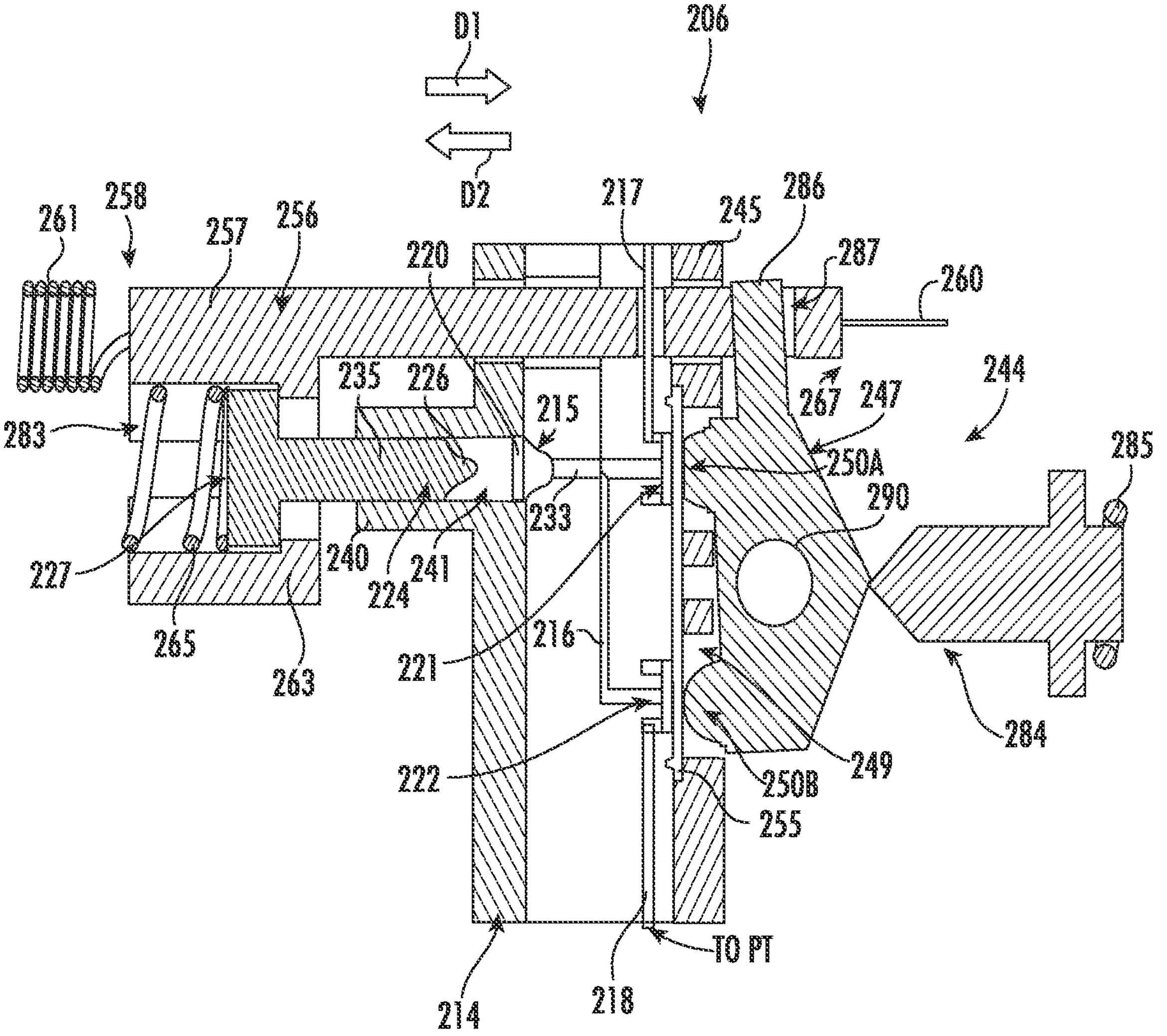
FIGS. 4A-4C illustrate side cross-sectional views of a drive mechanism of a delivery pump device according to embodiments of the present disclosure.
Figure 4B:
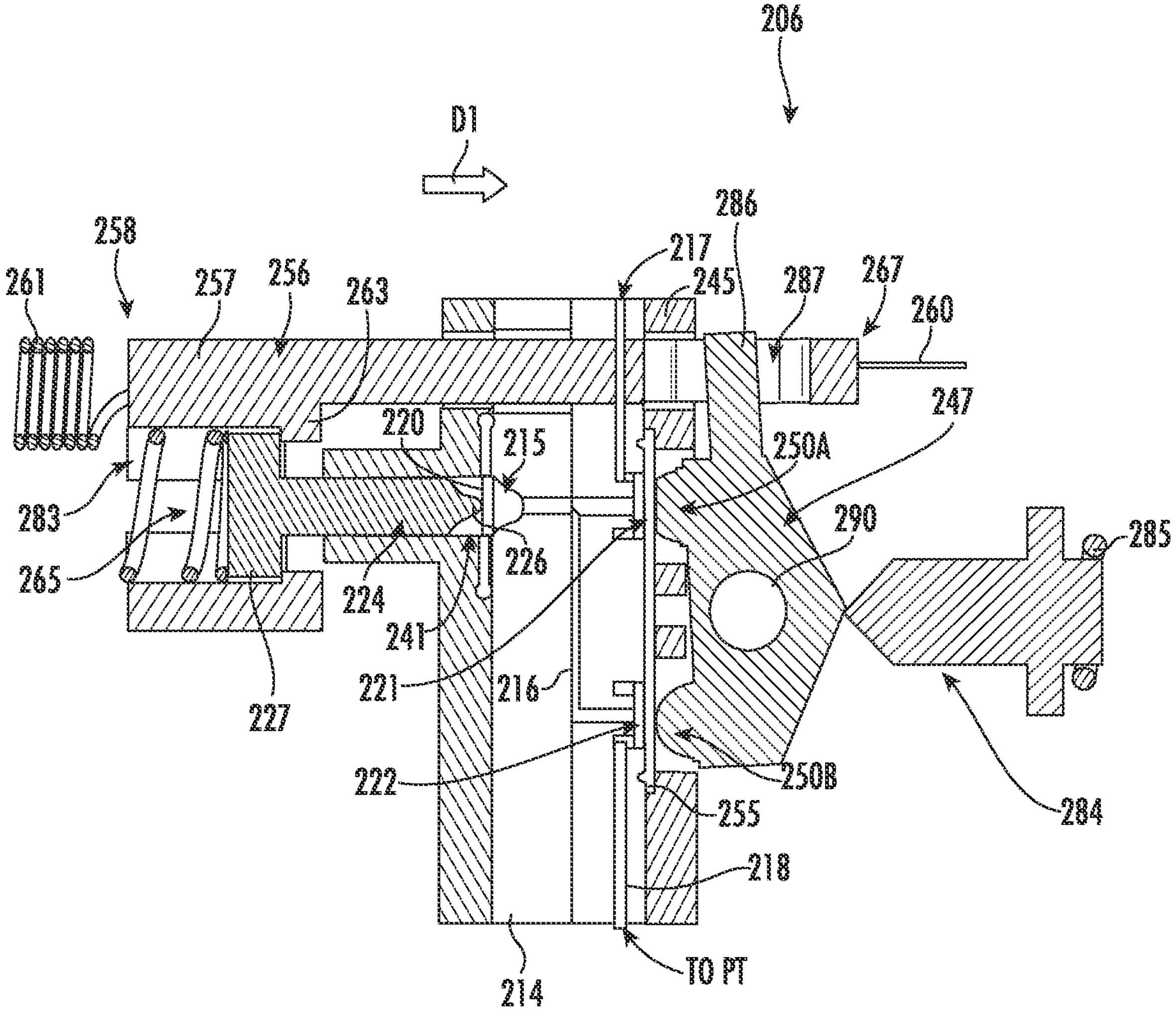
Figure 4C:
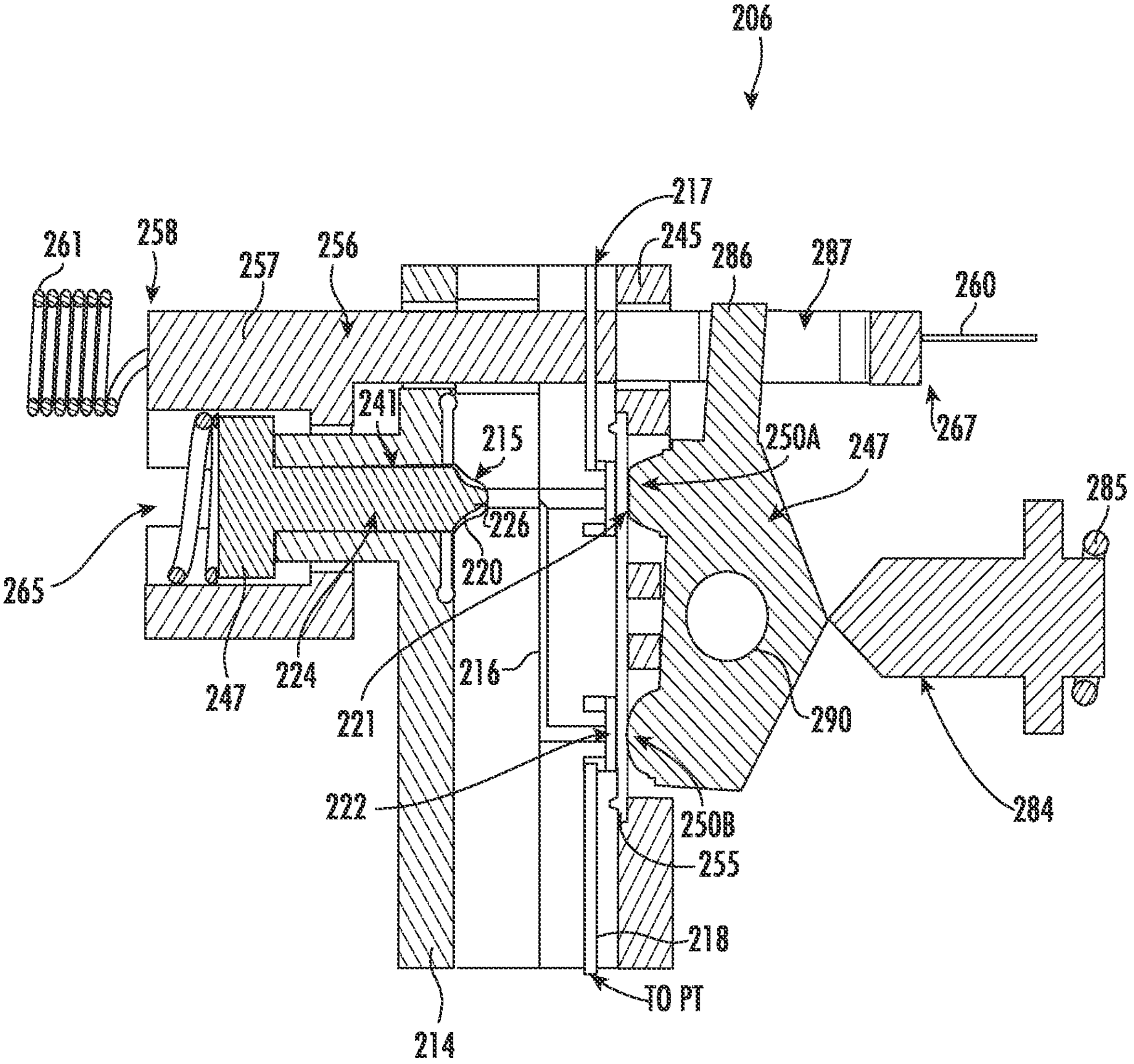

FIGS. 4A-4C illustrate an alternative drive mechanism 206 according to embodiments of the present disclosure. The drive mechanism 206 may be part of a delivery pump device, such as delivery pump device 105 of FIG. 1. As shown, the drive mechanism 206 may include a housing 214 defining a pump chamber 215, a channel chamber or pathway 216, an inlet channel 217 fluidly connected with a reservoir (not shown), and an outlet channel 218 for delivering a liquid drug to a patient, e.g., via a cannula. The inlet channel 217 may be connected with an inlet valve 221, and the outlet channel 218 may be connected with an outlet valve 222. In some embodiments, the pump chamber 215 and the second pathway 216 may be fluidly connected by an internal channel 233 through the housing 214. Although non-limiting, the pump chamber 215 may have a bell shape/profile to receive a correspondingly shaped tip 226 of a plunger 224.

As shown, the housing 214 may include a plunger cylinder 240 defining an internal plunger chamber 241 configured to receive a shaft 235 of the plunger 224. The plunger 224 may further include a flange 227 in contact with a plunger spring 265. The flange 227 and the plunger spring 265 may be positioned within a cavity 283 of a follower 256, wherein the follower 256 is coupled to the housing 214. In some embodiments, an engagement wall 263 of the follower 256 may be in contact with the flange 227 of the plunger 224.

As further shown, the drive mechanism 206 may include a resilient sealing member 220 positioned across the pump chamber 215, creating a liquid-tight seal between the internal plunger chamber 241 and the pump chamber 215. In some embodiments, the resilient sealing member 220 is directly coupled to the housing 214. Although non-limiting, the resilient sealing member 220 may be made from a shape memory polymer, such as a polymeric smart material, which has the ability to return from a temporary deformed/compressed shape to a permanent or natural, undeformed shape. For example, the straight/vertical configuration of the resilient sealing member 220 may correspond to its natural or permanent shape.

The drive mechanism 206 may further include a switching device 244 coupled to the housing 214. In some embodiments, the switching device 244 may be a mechanical toggle including a base 245, a rocker 247, and a bias 284. In some embodiments, the bias 284 is loaded by a spring 285. As shown, the rocker 247 may include a pair of legs 250A, 250B extending into corresponding openings 249 of the base 245. During operation, one of the legs 250A, 250B of the rocker 247 may be pressed against a second resilient sealing member 255 depending on the position of the rocker 247. Although non-limiting, the second resilient sealing member 155 may be made from a shape memory polymer, such as a polymeric smart material, which has the ability to return from a temporary deformed/compressed shape to a permanent or natural, undeformed shape. For example, the straight/horizontal configuration of the second resilient sealing member 255 may correspond to its natural or permanent shape.

As shown, an arm 286 of the rocker 247 may extend through an opening 287 of the follower 256. The follower 256 may include a body 257 having a first end 267 opposite a second end 258. Coupled to the first end 267 may be a first biasing device 260, (e.g., an SMA wire, motor with lead screw, or linear actuator), and coupled to the second end 258 may be a second biasing device 261 (e.g., a return spring). The first biasing device 260 may cause the follower 256 to move in a first direction 'D1', and the second biasing device 261 may cause the follower 256 to move in a second direction 'D2', opposite the first direction.

In the case the first biasing device 260 is an SMA wire, a power element (e.g., power element 132 in FIG. 1) may be activated to energize the SMA wire, which causes the SMA wire to change shape (e.g., contract). More specifically, the activated SMA wire begins to shorten, after having previously been passively relaxed, pulling the follower 256 and the plunger 224 along direction 'D1' as the SMA wire strives to return to its memorized or natural/pre-stressed shape and length. In various embodiments, contraction of the SMA wire may be controlled by increasing or decreasing heat generated by the power element. For example, a lower current supplied to the SMA wire may cause the follower 256 to move more slowly than a higher current.

At the stage demonstrated in FIG. 4A, the first biasing device 260 may be inactive, which allows the second biasing device 261 to pull the follower 256 along direction 'D2,' thus causing the rocker 247 to rotate (e.g. counterclockwise) about a center pin 290. Due to the force from the bias 284 on the leg 250A, the second resilient sealing member 255 may be deformed or depressed against the inlet valve 221 to create a liquid-tight seal therebetween, which prevents further flow of a liquid drug from the inlet channel 217. As further shown, the plunger 224 is retracted relative to the pump chamber 215 and the resilient sealing member 220, which may cause the liquid drug to fill the pump chamber 215. A force from the plunger spring 265 may maintain contact between the engagement wall 263 of the follower 256 and the flange 227 of the plunger 224 as the plunger 224 moves out of the plunger cylinder 240.

As demonstrated in FIG. 4B, the first biasing device 260 may be activated, e.g., in response to a current received from the power element, which causes the follower 256 to start moving along direction 'D1'. The plunger 224 moves together with the follower 256, causing the plunger 224 to travel within the internal plunger chamber 241 and towards the resilient sealing member 220. Activation of the first biasing device 260 continues, as demonstrated in FIG. 4C, which causes the tip 226 of the plunger 224 and the resilient sealing member 220 to fully enter the pump chamber 215 and expel the liquid drug therefrom. A force from the plunger 224 may cause the liquid drug to travel through the second pathway 216, through the outlet valve 222, and out through the outlet channel 218. As the rocker 247 is further rotated by the follower 256, the inlet valve 221 is opened and the outlet valve 222 is closed, thus preventing the liquid from exiting through the outlet channel 218.

Figure 5:
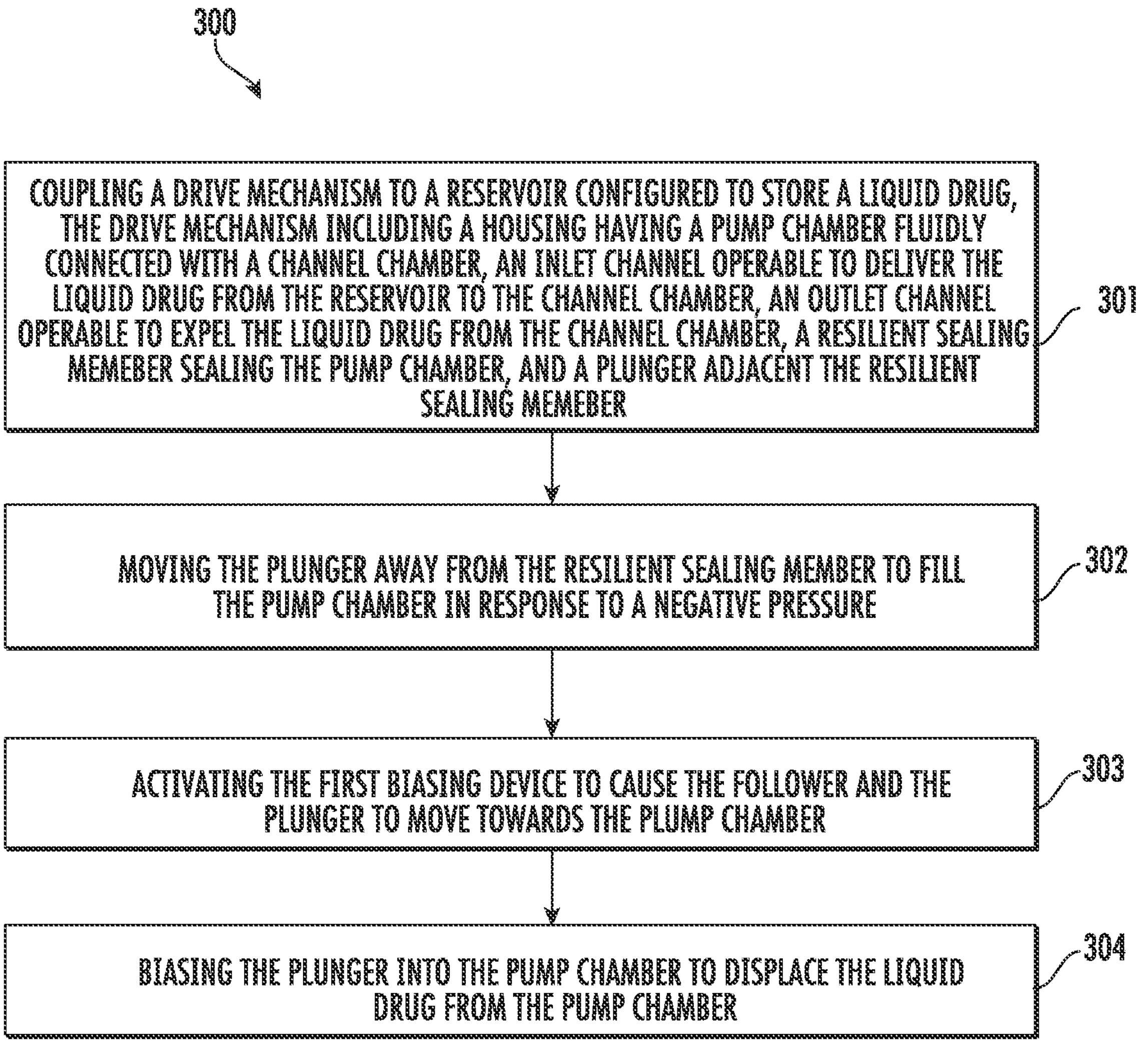
FIG. 5 illustrates a process flow of a method according to embodiments of the present disclosure.

FIG. 5 illustrates an example process 300 according to embodiments of the present disclosure. At block 301, the process 300 may include coupling a drive mechanism to a reservoir configured to store a liquid drug. In some embodiments, the drive mechanism is part of a wearable drug delivery device. The drive mechanism may include a housing having a pump chamber fluidly connected with a channel chamber, an inlet channel operable to deliver the liquid drug from the reservoir to the channel chamber, and an outlet channel operable to expel the liquid drug from the channel chamber. The drive mechanism may further include a resilient sealing member sealing the pump chamber, and a plunger adjacent the resilient sealing member. In some embodiments, the resilient sealing member are directly attached/coupled to one another.

At block 302, the process 300 may include moving the plunger away from the resilient sealing member to fill the pump chamber, while the outlet channel is closed, in response to a negative pressure created within the pump chamber. In some embodiments, the plunger is coupled to a follower, which is biasable in a first direction by a first biasing device and in a second direction by a second biasing device. In some embodiments, the first biasing device is an SMA wire, wherein deactivating the SMA wire may cause the follower and the plunger to move away from the housing.

At block 303, the process 300 may further include activating the first biasing device to cause the follower and the plunger to move towards the pump chamber. In some embodiments, a mechanical rocker device transitions from a first position in which a second resilient sealing member is biased against the outlet channel, to a second position in which the second resilient sealing member is biased against the inlet channel. In some embodiments, the follower is coupled to the mechanical rocker device, wherein movement of the follower relative to the housing causes the mechanical rocker device to transition between the first and second positions.

At block 304, the process 300 may further include biasing the plunger into the pump chamber to displace the liquid drug from the pump chamber. In some embodiments, the liquid drug is forced from the pump chamber, through an internal channel of the housing and the channel chamber, and out through the outlet channel for delivery to patient, e.g., via a cannula. The SMA wire may then be de-activated again to move the plunger and the resilient sealing member from within the pump chamber to a neutral/natural position, to draw in more liquid drug, thus repeating the cycle. In some embodiments, deactivation of the SMA wire, e.g., by a controller, may occur following expiration of a predetermined time period triggered by the initial activation of the SMA wire. The predetermined time period may be sufficient to allow a controlled dose (e.g., 0.05 mL or 0.025 mL) of the liquid drug to enter and then be extinguished from the pump chamber. Alternatively, deactivation may be triggered when the resilient sealing member reaches a particular position within the pump chamber, or when the plunger reaches a particular position within the plunger chamber. For example, electrodes may be placed within a flange of the plunger and in the end of the plunger cylinder to determine a relative position of the flange, which may cause the controller of the drug delivery device to take a certain action, such as de-activation of the SMA wire.

As used herein, the algorithms or computer applications that manage blood glucose levels and insulin therapy may be referred to as an "artificial pancreas" algorithm-based system, or more generally, an artificial pancreas (AP) application. An AP application may be programming code stored in a memory device and that is executable by a processor, controller or computer device.

The techniques described herein for a drug delivery system (e.g., the system 100 or any components thereof) may be implemented in hardware, software, or any combination thereof. Any component as described herein may be implemented in hardware, software, or any combination thereof. For example, the system 100 or any components thereof may be implemented in hardware, software, or any combination thereof. Software related implementations of the techniques described herein may include, but are not limited to, firmware, application specific software, or any other type of computer readable instructions that may be executed by one or more processors. Hardware related implementations of the techniques described herein may include, but are not limited to, integrated circuits (ICs), application specific ICs (ASICs), field programmable arrays (FPGAs), and/or programmable logic devices (PLDs). In some examples, the techniques described herein, and/or any system or constituent component described herein may be implemented with a processor executing computer readable instructions stored on one or more memory components.

Some examples of the disclosed devices may be implemented, for example, using a storage medium, a computer-readable medium, or an article of manufacture which may store an instruction or a set of instructions that, if executed by a machine (i.e., processor or controller), may cause the machine to perform a method and/or operation in accordance with examples of the disclosure. Such a machine may include, for example, any suitable processing platform, computing platform, computing device, processing device, computing system, processing system, computer, processor, or the like, and may be implemented using any suitable combination of hardware and/or software. The computer-readable medium or article may include, for example, any suitable type of memory unit, memory, memory article, memory medium, storage device, storage article, storage medium and/or storage unit, for example, memory (including non-transitory memory), removable or non-removable media, erasable or non-erasable media, writeable or re-writeable media, digital or analog media, hard disk, floppy disk, Compact Disk Read Only Memory (CD-ROM), Compact Disk Recordable (CD-R), Compact Disk Rewriteable (CD-RW), optical disk, magnetic media, magneto-optical media, removable memory cards or disks, various types of Digital Versatile Disk (DVD), a tape, a cassette, or the like. The instructions may include any suitable type of code, such as source code, compiled code, interpreted code, executable code, static code, dynamic code, encrypted code, programming code, and the like, implemented using any suitable high-level, low-level, object-oriented, visual, compiled and/or interpreted programming language. The non-transitory computer readable medium embodied programming code may cause a processor when executing the programming code to perform functions, such as those described herein.

Certain examples of the present disclosed subject matter were described above. It is, however, expressly noted that the present disclosed subject matter is not limited to those examples, but rather the intention is that additions and modifications to what was expressly described herein are also included within the scope of the disclosed subject matter. Moreover, it is to be understood that the features of the various examples described herein were not mutually exclusive and may exist in various combinations and permutations, even if such combinations or permutations were not made express herein, without departing from the spirit and scope of the disclosed subject matter. In fact, variations, modifications, and other implementations of what was described herein will occur to those of ordinary skill in the art without departing from the spirit and the scope of the disclosed subject matter. As such, the disclosed subject matter is not to be defined only by the preceding illustrative description.

Program aspects of the technology may be thought of as "products" or "articles of manufacture" typically in the form of executable code and/or associated data that is carried on or embodied in a type of machine readable medium. Storage type media include any or all of the tangible memory of the computers, processors or the like, or associated modules thereof, such as various semiconductor memories, tape drives, disk drives and the like, which may provide non-transitory storage at any time for the software programming. It is emphasized that the Abstract of the Disclosure is provided to allow a reader to quickly ascertain the nature of the technical disclosure. It is submitted with the understanding that it will not be used to interpret or limit the scope or meaning of the claims. In addition, in the foregoing Detailed Description, various features are grouped together in a single example for streamlining the disclosure. This method of disclosure is not to be interpreted as reflecting an intention that the claimed examples require more features than are expressly recited in each claim. Rather, as the following claims reflect, inventive subject matter lies in less than all features of a single disclosed example. Thus, the following claims are hereby incorporated into the Detailed Description, with each claim standing on its own as a separate example. In the appended claims, the terms "including" and "in which" are used as the plain-English equivalents of the respective terms "comprising" and "wherein," respectively. Moreover, the terms "first," "second," "third," and so forth, are used merely as labels and are not intended to impose numerical requirements on their objects.

The foregoing description of example examples has been presented for the purposes of illustration and description. It is not intended to be exhaustive or to limit the present disclosure to the precise forms disclosed. Many modifications and variations are possible in light of this disclosure. It is intended that the scope of the present disclosure be limited not by this detailed description, but rather by the claims appended hereto. Future filed applications claiming priority to this application may claim the disclosed subject matter in a different manner and may generally include any set of one or more limitations as variously disclosed or otherwise demonstrated herein.

What is claimed is:

1. A wearable therapeutic agent delivery device, comprising:

a reservoir configured to store a liquid therapeutic agent;

a delivery pump device including a drive mechanism coupled to the reservoir for receiving the liquid therapeutic agent, the drive mechanism comprising:

a housing comprising:

a pump chamber fluidly connected with a channel chamber;

an inlet channel operable to deliver the liquid therapeutic agent from the reservoir to the channel chamber; and an outlet channel operable to expel the liquid therapeutic agent from the channel chamber;

a resilient sealing member sealing the pump chamber;

a plunger operable to enter the pump chamber to displace the liquid therapeutic agent from the pump chamber;

a second resilient sealing member positioned within the channel chamber, wherein the second resilient sealing member is operable to seal the inlet channel and the outlet channel; and a switching device, wherein in a first position the switching device biases the second resilient sealing member against an entrance of the inlet channel, and wherein in a second position the switching device biases the second resilient sealing member against an entrance of the outlet channel.

2. The wearable therapeutic agent delivery device of claim 1, further comprising a follower coupled to the switching device, wherein movement of the follower relative to the housing causes the switching device to move between the first and second positions.

3. The wearable therapeutic agent delivery device of claim 2, further comprising a biasing device coupled to the follower, wherein the biasing device causes the follower to move relative to the housing.

4. The wearable therapeutic agent delivery device of claim 3, wherein the biasing device is a shape memory alloy wire.

5. The wearable therapeutic agent delivery device of claim 4, further comprising a power source coupled to the shape memory alloy wire, wherein power from the power source causes the shape memory alloy wire to contract.

6. The wearable therapeutic agent delivery device of claim 5, further comprising a controller communicatively coupled to the power source, wherein the controller is operable to:

receive an input indicating an automated insulin delivery (AID) application setting; and in response to the input, activate the power source.

7. The wearable therapeutic agent delivery device of claim 3, further comprising a return spring coupled to the follower, wherein the biasing device causes the follower to move in a first direction, and wherein the return spring causes the follower to move in a second direction, opposite the first direction.

8. The wearable therapeutic agent delivery device of claim 3, further comprising a plunger spring in abutment with the plunger and with the follower, wherein the plunger spring is operable to cause the plunger to enter the pump chamber as the follower moves towards the housing.

9. The wearable therapeutic agent delivery device of claim 1, wherein the plunger is positioned within a plunger chamber, and wherein the resilient sealing member is positioned between the plunger chamber and the pump chamber.

10. The wearable therapeutic agent delivery device of claim 1, wherein in the first position the switching device biases the second resilient sealing member against an entrance of the inlet channel such that the second resilient sealing member blocks fluid flow through the inlet channel while permitting fluid flow through the outlet channel, and wherein in the second position the switching device biases the second resilient sealing member against an entrance of the outlet channel such that the second resilient sealing member blocks fluid flow through the outlet channel while permitting fluid flow through the inlet channel.

11. A drive mechanism of a wearable therapeutic agent delivery device, the drive mechanism comprising:

a housing comprising:

a pump chamber fluidly connected with a channel chamber;

an inlet channel operable to deliver a liquid therapeutic agent from a reservoir to the channel chamber; and an outlet channel operable to expel the liquid therapeutic agent from the channel chamber;

a resilient sealing member sealing the pump chamber; and a plunger operable to enter the pump chamber to displace the liquid therapeutic agent from the pump chamber;

a second resilient sealing member positioned within the channel chamber, wherein the second resilient sealing member is operable to seal the inlet channel and the outlet channel; and a switching device, wherein in a first position the switching device biases the second resilient sealing member against an entrance of the inlet channel, and wherein in a second position the switching device biases the second resilient sealing member against an entrance of the outlet channel.

12. The drive mechanism of claim 11, wherein the switching device is a mechanical rocker device and further comprising:

a follower coupled to the mechanical rocker device, wherein movement of the follower relative to the housing causes the mechanical rocker device to move between the first and second positions; and a shape memory alloy wire coupled to the follower, wherein the shape memory alloy wire causes the follower to move relative to the housing.

13. The drive mechanism of claim 12, further comprising a return spring coupled to the follower, wherein the return spring causes the follower to move in a first direction, and wherein the return spring causes the follower to move in a second direction, opposite the first direction.

14. A method, comprising:

coupling a drive mechanism to a reservoir configured to store a liquid therapeutic agent, the drive mechanism comprising:

a housing comprising:

a pump chamber fluidly connected with a channel chamber;

an inlet channel operable to deliver the liquid therapeutic agent from the reservoir to the channel chamber;

an outlet channel operable to expel the liquid therapeutic agent from the channel chamber;

a resilient sealing member sealing the pump chamber;

a plunger operable to enter the pump chamber to displace the liquid therapeutic agent from the pump chamber;

a second resilient sealing member positioned within the channel chamber, wherein the second resilient sealing member is operable to seal the inlet channel and the outlet channel; and a switching device, wherein in a first position the switching device biases the second resilient sealing member against an entrance of the inlet channel, and wherein in a second position the switching device biases the second resilient sealing member against an entrance of the outlet channel; and biasing the plunger into the pump chamber to displace the liquid therapeutic agent from the pump chamber.

15. The method of claim 14, further comprising:

coupling the plunger to a follower; and coupling a shape memory alloy wire to the follower, wherein biasing the plunger comprises activating the shape memory alloy wire to bias the follower and the plunger towards the housing.

16. The method of claim 15, further comprising deactivating the shape memory alloy wire to bias the follower and the plunger away from the housing, wherein biasing the plunger away from the housing causes the liquid therapeutic agent to enter the pump chamber through the inlet channel.

17. The method of claim 15, further comprising:

positioning the second resilient sealing member within the channel chamber;

coupling the switching device to the follower; and biasing the follower relative to the housing to cause the switching device to transition between the first position and the second position.

* * * * *